(12) United States Patent
Zhang et al.

(10) Patent No.: US 11,844,715 B2
(45) Date of Patent: Dec. 19, 2023

(54) ADJUSTABLE NECK SUPPORT

(71) Applicant: Guangzhou New Design Biotechnology Co. Ltd., Guangzhou (CN)

(72) Inventors: Shaowei Zhang, Guangzhou (CN); Sile Zou, Guangzhou (CN); Weijie Shen, Guangzhou (CN); Jiehong Lin, Guangzhou (CN); Yuhui Ou, Guangzhou (CN)

(73) Assignee: Guangzhou New Design Biotechnology Co. Ltd., Guangzhou (CN)

( * ) Notice: Subject to any disclaimer, the term of this patent is extended or adjusted under 35 U.S.C. 154(b) by 0 days.

(21) Appl. No.: 18/363,618

(22) Filed: Aug. 1, 2023

(65) Prior Publication Data

US 2023/0372138 A1 Nov. 23, 2023

Related U.S. Application Data

(63) Continuation of application No. PCT/CN2022/086986, filed on Apr. 15, 2022.

(30) Foreign Application Priority Data

Dec. 31, 2021 (CN) .......................... 202111666094.2

(51) Int. Cl.
A61F 5/055 (2006.01)
(52) U.S. Cl.
CPC .................... A61F 5/055 (2013.01)
(58) Field of Classification Search
CPC .... A61F 5/055; A61F 5/05; A61F 5/04; A61F 5/01; A61F 5/00; A61F 5/05883;
(Continued)

(56) References Cited

U.S. PATENT DOCUMENTS

2019/0350740 A1* 11/2019 Maher ..................... A61F 5/055
2022/0039990 A1* 2/2022 Lin ......................... A61F 5/026
(Continued)

FOREIGN PATENT DOCUMENTS

| CN | 206304012 U | 7/2017 |
| CN | 110812698 A | 2/2020 |

(Continued)

OTHER PUBLICATIONS

First Office Action issued in counterpart Chinese Patent Application No. 202111666094.2, dated Aug. 26, 2022.

Primary Examiner — Tarla R Patel
(74) Attorney, Agent, or Firm — Westbridge IP LLC

(57) ABSTRACT

An adjustable neck support includes a neck holder front support, a left side plate, a right side plate, a lower jaw holder plate, and a height adjustment knob. The left side plate is movably connected at a left end of the neck holder front support, the right side plate is movably connected at a right end of the neck holder front support, the lower jaw holder plate is connected between the left side plate and the right side plate, and the height adjustment knob is mounted on the neck holder front support. The height adjustment knob includes an operating cover and a winding post connected to the operating cover, the winding post being mounted in the neck holder front support. The adjustable neck support provided by the application is smooth in height adjustment operation, easy to operate, and long in service life.

4 Claims, 8 Drawing Sheets

(58) Field of Classification Search
CPC .. A61F 5/058; A61F 5/05833; A61F 5/05816;
A61F 5/3707; A61F 5/37
See application file for complete search history.

(56) References Cited

U.S. PATENT DOCUMENTS

| 2022/0125615 | A1* | 4/2022 | Maher | A61F 7/10 |
| 2022/0287865 | A1* | 9/2022 | Tate Morgan | A61F 5/055 |

FOREIGN PATENT DOCUMENTS

| CN | 210170255 U | 3/2020 |
| CN | 210843920 U | 6/2020 |
| CN | 213190402 U | 5/2021 |

* cited by examiner

ADJUSTABLE NECK SUPPORT

CROSS-REFERENCE TO RELATED APPLICATIONS

This application is a continuation of International Application No. PCT/CN2022/086986, filed on Apr. 15, 2022, which claims priority to Chinese Patent Application No. 202111666094.2, filed on Dec. 31, 2021. All of the aforementioned applications are incorporated herein by reference in their entireties.

TECHNICAL FIELD

The application relates to the technical field of medical rehabilitation assistive appliances, in particular to an adjustable neck support.

BACKGROUND

A neck support is one of commonly used assistive devices for the treatment and rehabilitation of cervical diseases in order to make the cervical spine obtain an external support and be in a stable state, and is generally configured to fix and restrict the movement of the neck of a patient, support the head, relieve local pressure, relax muscles, and alleviate pain or perform postoperative rehabilitation.

However, existing neck supports are generally of a fixed or adjustable structure. The neck support of the fixed structure is not suitable for patients with different neck lengths due to the incapability of adjusting the height. Existing adjustable neck supports are generally of a gear and rack structure, and often require a relatively large external force to operate due to the meshing friction of a gear and a rack when the height is adjusted, so that the operation is not smooth and laborious. Furthermore, after a long time of use, the gear and the rack are worn to varying degrees, and are prone to slip after wear, so that the neck support is short in service life.

SUMMARY

The application provides an adjustable neck support, which is smooth in height adjustment operation and easy to operate, and effectively prolongs the service life.

The application adopts the following technical solution that: an adjustable neck support includes a neck holder front support, a left side plate, a right side plate, a lower jaw holder plate, and a height adjustment knob. The left side plate and the right side plate are movably connected at a left end and a right end of the neck holder front support respectively, the lower jaw holder plate is connected between the left side plate and the right side plate, and the height adjustment knob is mounted on the neck holder front support. The height adjustment knob includes an operating cover and a winding post connected to the operating cover. The winding post is mounted in the neck holder front support, and the operating cover exposes the neck holder front support.

A first sliding block and a second sliding block are slidably mounted in the neck holder front support, the first sliding block is provided with a first connecting head, and the second sliding block is provided with a second connecting head. The first connecting head is slidably connected to the left end of the neck holder front support and the left side plate, the second connecting head is slidably connected to the right end of the neck holder front support and the right side plate, a first cable and a second cable are wound on the winding post, both ends of the first cable are fixed to the first sliding block, and both ends of the second cable are fixed to the second sliding block.

Further, the winding post is provided with a limited block and an extension part. The limited block is matched with the neck holder front support, and the operating cover is connected to the limited block. A first winding groove and a second winding groove are formed at both sides of the extension part respectively. The winding post is provided with a first threading hole and a second threading hole. The first threading hole is located in the first winding groove, the first cable penetrates through the first threading hole, and the first cable is wound in the first winding groove. The second threading hole is located in the second winding groove, the second cable penetrates through the second threading hole, and the second cable is wound in the second winding groove.

Further, the limited block is provided with two mounting grooves and two elastic grooves. The two mounting grooves are oppositely arranged, the two elastic grooves are oppositely arranged, and each elastic groove is arranged adjacent to each mounting groove. A connecting part protrudes from the bottom of the operating cover, the connecting part is provided with four limited posts, two of the limited posts are located in the two mounting grooves respectively, and the other two are located in the two elastic grooves respectively.

Further, a notch of each elastic groove is provided with a convex tooth, and the neck holder front support is provided with an internal spline matched with the convex tooth.

Further, the neck holder front support is provided with a first chute and a second chute, and the winding post is located between the first chute and the second chute. The first sliding block is slidably mounted in the first chute, and the second sliding block is slidably mounted in the second chute.

Further, the first sliding block is provided with two first joint pins. One first joint pin is located at the tail of the first sliding block, and the other first joint pin is located in the middle of the first sliding block, and both ends of the first cable are fixed to the two first joint pins respectively.

Further, the second sliding block is provided with two second joint pins. One second joint pin is located at the tail of the second sliding block, and the other second joint pin is located in the middle of the second sliding block, and both ends of the second cable are fixed to the two second joint pins respectively.

Further, the first winding groove is provided with a first limiting groove, a first limit sleeve is mounted on the first cable, and the first limit sleeve is contained in the first limiting groove. The second winding groove is provided with a second limiting groove, a second limit sleeve is mounted on the second cable, and the second limit sleeve is contained in the second limiting groove.

Further, the neck holder front support includes a bottom shell and an outer cover connected to the bottom shell. The connecting part is provided with a mounting hole, a nut is mounted in the mounting hole, and the winding post is mounted on the bottom shell. A screw penetrates through the winding post, one end of the screw abuts against the bottom shell, and the other end is connected to the nut, and the operating cover abuts against the outer cover.

Further, one end of the left side plate is rotatably connected to the left end of the bottom shell, and the other end is provided with a left chute. One end of the right side plate is rotatably connected to the right end of the bottom shell, and the other end is provided with a right chute. The left end of the bottom shell is provided with a third chute, and the right end is provided with a fourth chute. The first connecting head penetrates through the third chute and the left chute, one face of the first connecting head abuts against the left end of the bottom shell, and the other face abuts against the left side plate. The second connecting head penetrates through the fourth chute and the right chute, one face of the second connecting head abuts against the right end of the bottom shell, and the other face abuts against the right side plate.

Compared with the related art, according to the adjustable neck support provided by the application, the height adjustment knob is provided with the first cable and the second cable, and the first sliding block and the second sliding block are slidably arranged in the neck holder front support. The first cable is connected to the first sliding block, the first sliding block is connected to the left side plate, the second cable is connected to the second sliding block, and the second sliding block is connected to the right side plate. When the height is adjusted, through the rotation of the operating cover, the winding post is driven to rotate to pull both ends of the first cable and both ends of the second cable, so that the first sliding block and the second sliding block slide in opposite directions in the neck holder front support respectively, thereby synchronously pushing up or pulling down the left side plate and the right side plate. Then the left side plate and the right side plate push or pull the lower jaw holder plate to realize the height adjustment of the neck support, so that the neck support is suitable for patients with different neck lengths. Compared with a traditional gear and rack adjustment structure, the smoothness of operation is effectively improved, so that the height adjustment is easier to operate, and the service life of the neck support is prolonged.

BRIEF DESCRIPTION OF THE DRAWINGS

The drawings are used to provide a further understanding of the application, constitute a part of the specification, and used to explain the application together with the following specific implementation mode, but not to limit the application. In the drawings.

DETAILED DESCRIPTION OF THE EMBODIMENTS

The specific implementation modes of the application are elaborated in detail below with reference to the drawings. It is to be understood that the specific implementation modes described herein are only used to describe and explain the application, but are not intended to limit the application.

Embodiment 1

Figure 1:
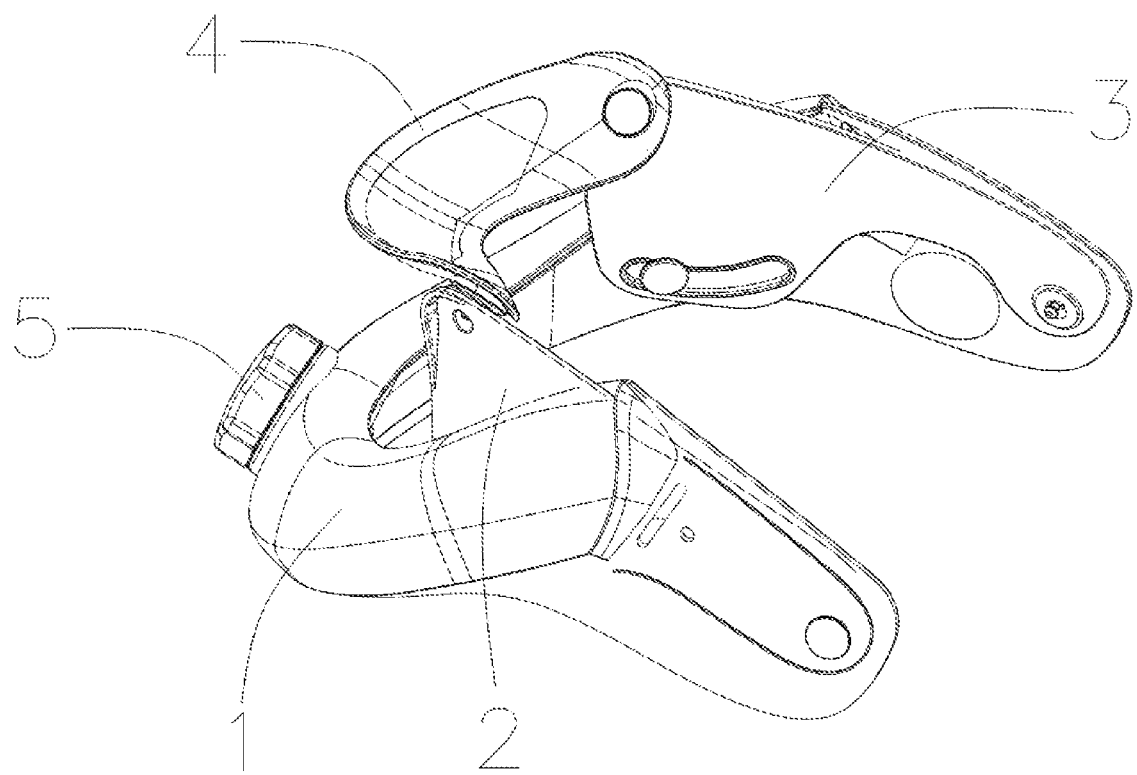
FIG. 1 is a stereoscopic combination diagram of an adjustable neck support of the application.
Figure 4:
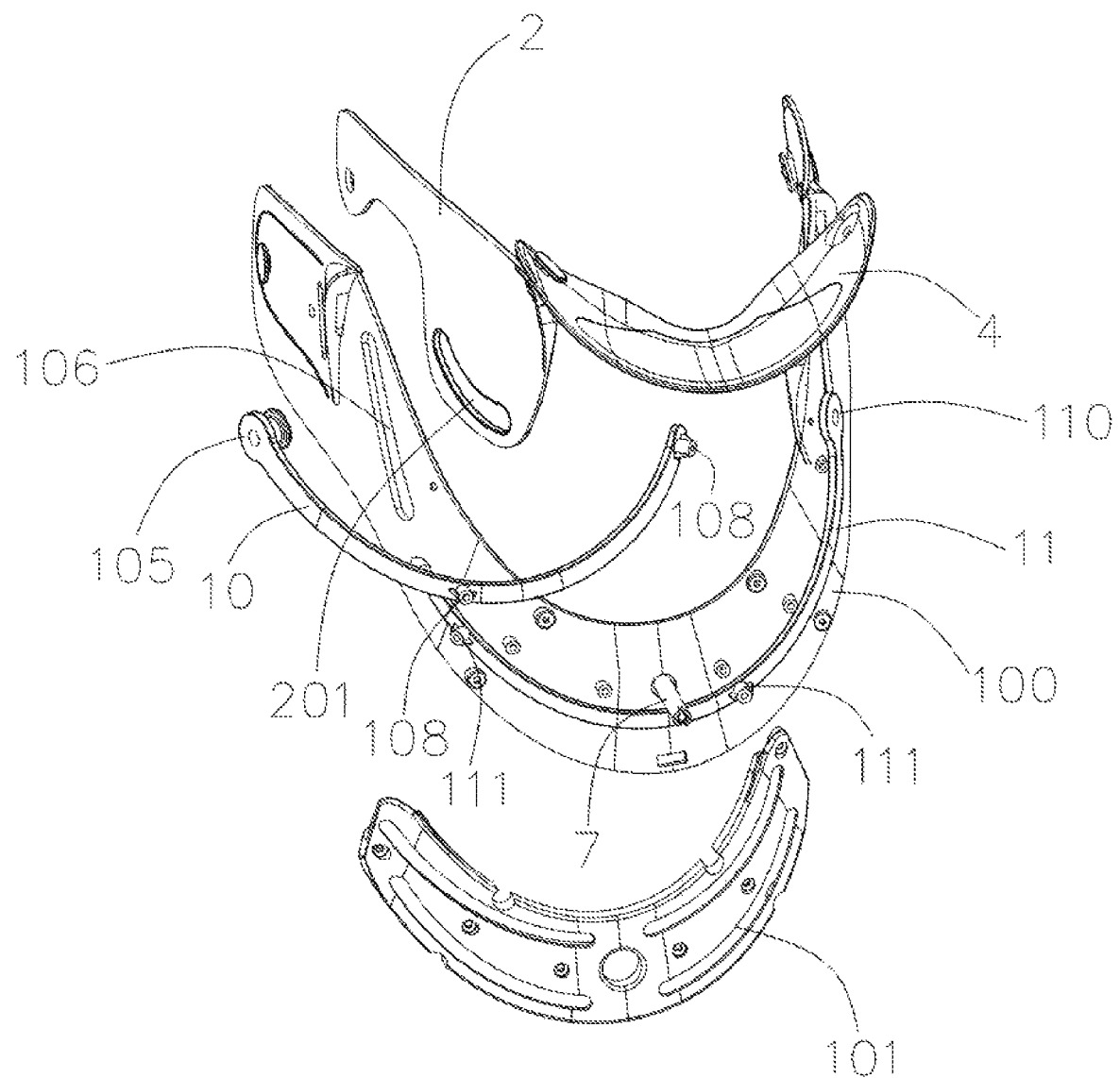
FIG. 4 is another stereoscopic exploded view of an adjustable neck support of the application.
Figure 5:
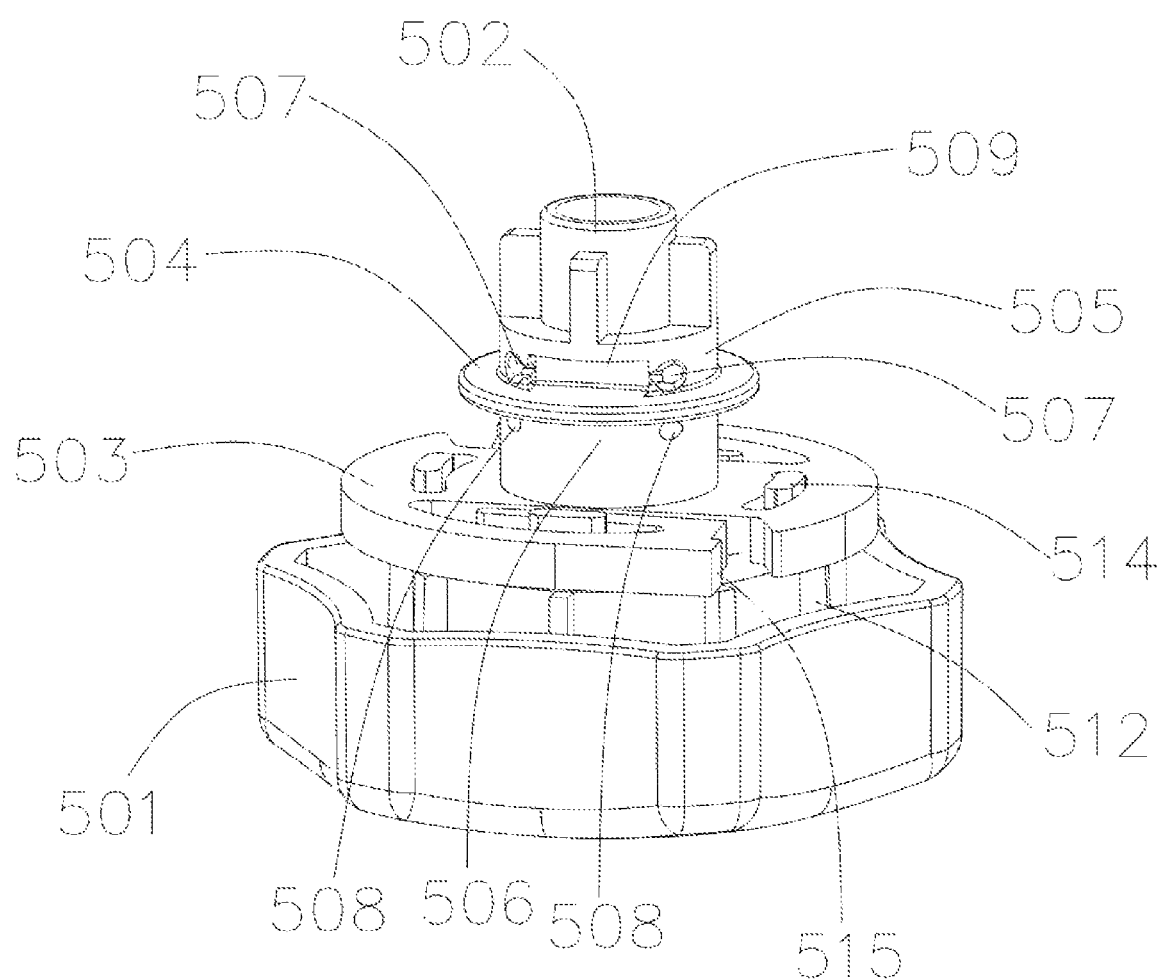
FIG. 5 is a stereoscopic combination diagram of a height adjustment knob of the application.
Figure 6:
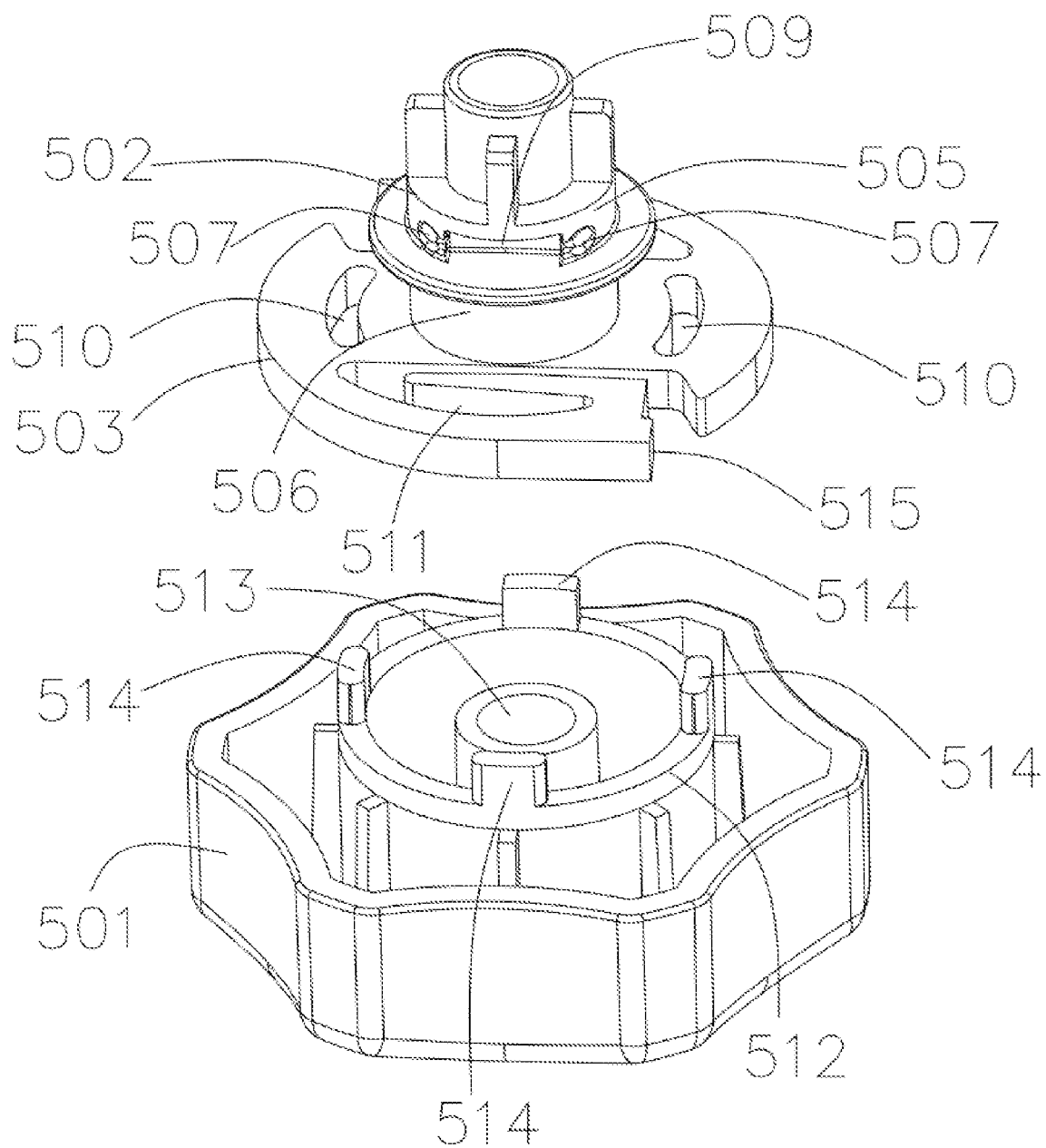
FIG. 6 is a stereoscopic exploded view of a height adjustment knob of the application.
Figure 7:
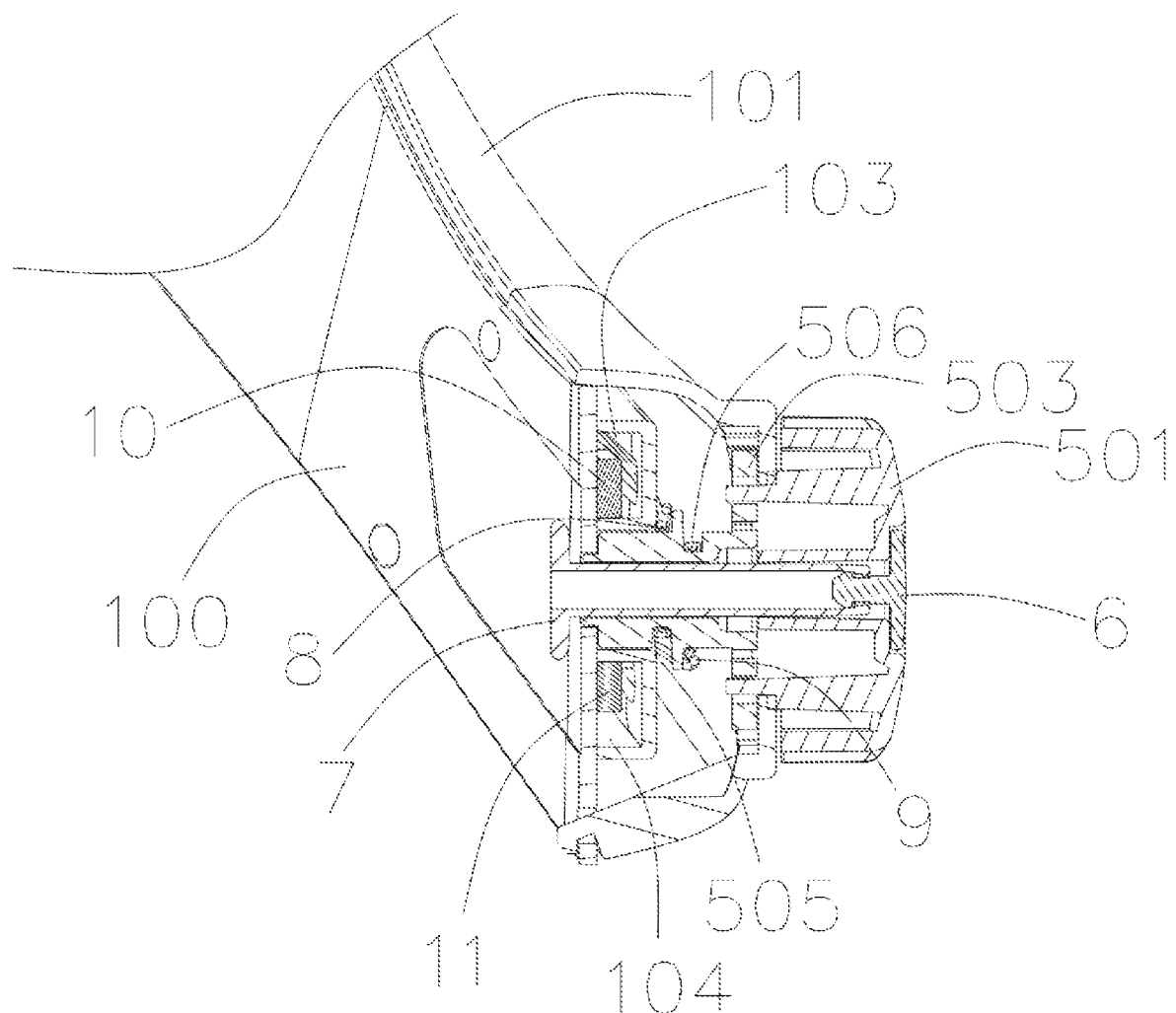
FIG. 7 is a partial sectional view of an adjustable neck support of the application.
Figure 8:
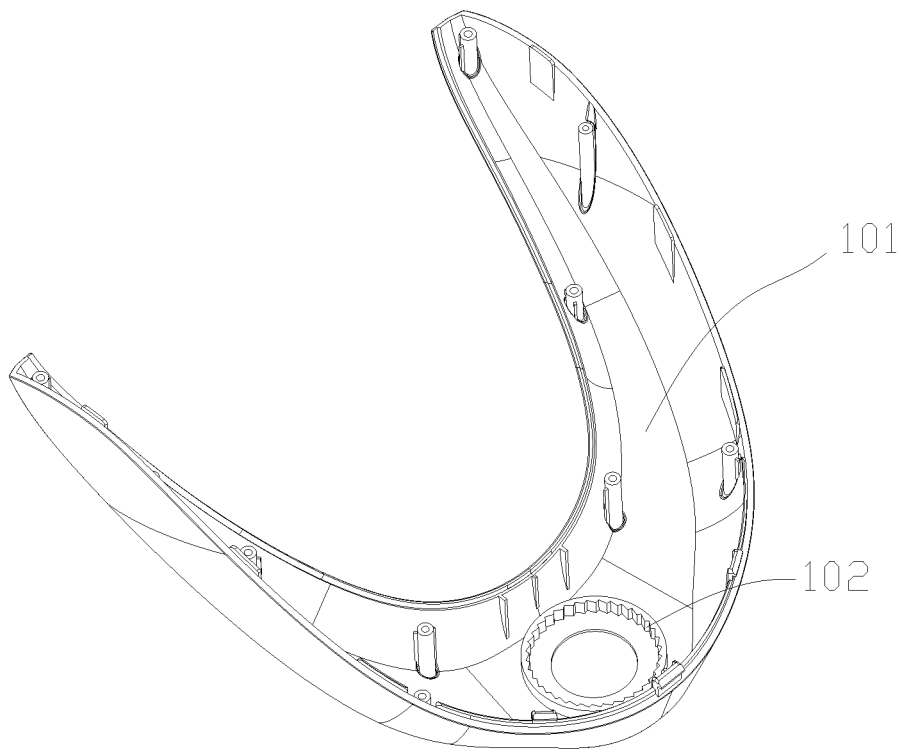
FIG. 8 is a stereogram of an outer cover of the application.

As shown in FIG. 1 and FIG. 4, an adjustable neck support provided by the application includes a neck holder front support 1, a left side plate 2, a right side plate 3, a lower jaw holder plate 4, and a height adjustment knob 5. The left side plate 2 is movably connected at a left end of the neck holder front support 1, the right side plate 3 is movably connected at a right end of the neck holder front support 1, and the lower jaw holder plate 4 is connected between the left side plate 2 and the right side plate 3. The height adjustment knob 5 is mounted on the neck holder front support 1, and the height adjustment knob 5 is mechanically connected to the left side plate 2 and the right side plate 3. Through the height adjustment knob 5, the height of the left side plate 2 and the height of the right side plate 3 are adjusted, so as to adjust the height of the lower jaw holder plate 4, so that the neck support is suitable for patients with different neck lengths.

As shown in FIG. 4 to FIG. 7, the neck holder front support 1 includes a bottom shell 100 and an outer cover 101 connected to the bottom shell 100. The height adjustment knob 5 is mounted on the bottom shell 100 and the outer cover 101 through a nut 6 and a bolt 7. The height adjustment knob 5 includes an operating cover 501 and a winding post 502. The nut 6 is mounted on the operating cover 501, and the winding post 502 is mounted on the bottom shell 100. The bolt 7 penetrates through the winding post 502, one end of the bolt 7 abuts against the bottom shell 100, the other end of the bolt 7 is connected to the nut 6, and the operating cover 501 abuts against the outer cover 101. Therefore, the height adjustment knob 5 is mounted on the neck holder front support 1.

Figure 9:
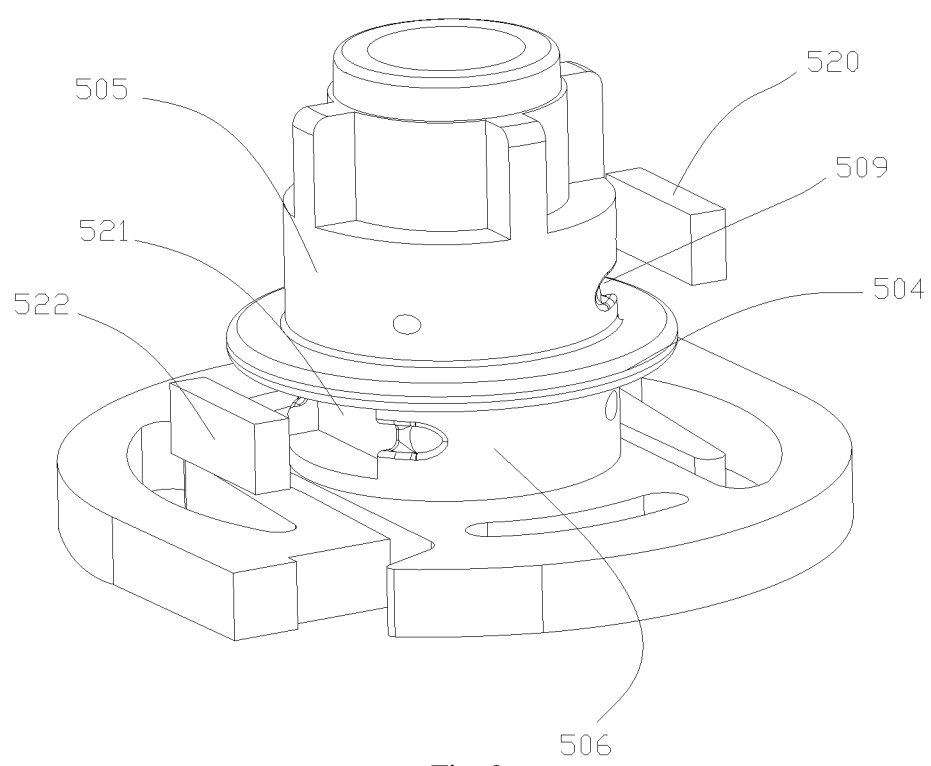
FIG. 9 is a schematic structural diagram of a second limit sleeve and a second limiting groove of the application.

Further, one end, close to the outer cover 101, of the winding post 502 is provided with a limited block 503, and the other end is provided with an extension part 504. A first winding groove 505 and a second winding groove 506 are formed at both sides of the extension part 504 respectively. The winding post 502 is provided with a first threading hole 507 and a second threading hole 508. The first threading hole 507 is located in the first winding groove 505, and configured to allow the first cable 8 to penetrate through, and then wind the first cable 8 in the first winding groove 505. The second threading hole 508 is located in the second winding groove 506, and configured to allow the second cable 9 to penetrate through, and then wind the second cable 9 in the second winding groove 506. In addition, the first winding groove 505 is provided with a first limiting groove 509, a first limit sleeve (as shown in FIG. 9) is mounted on the first cable 8, and the first limit sleeve 520 is contained in the first limiting groove 509, so as to effectively avoid the first cable 8 moving. The second winding groove 506 is provided with a second limiting groove 521 (as shown in FIG. 9), a second limit sleeve 522 (as shown in FIG. 9) is mounted on the second cable 9, and the second limit sleeve 522 is contained in the second limiting groove 521 (as shown in FIG. 9), so as to effectively avoid the second cable 9 moving.

The limited block 503 is provided with two mounting grooves 510 and two elastic grooves 511. The two mounting grooves 510 are oppositely arranged, the two elastic grooves 511 are oppositely arranged, and each elastic groove 511 is arranged adjacent to each mounting groove 510. A connecting part 512 protrudes from the bottom of the operating cover 501, a mounting hole 513 is arranged in the middle of the connecting part 512, and the nut 6 is mounted in the mounting hole 513. The connecting part 512 is provided with four limited posts 514, two of the limited posts 514 are located in the two mounting grooves 510 respectively, and correspond to the two mounting grooves 510 one by one, and the other two limited posts 514 are located in the two elastic grooves 511 respectively, and the two limited posts 514 correspond to the two elastic grooves 511 one by one, so that the operating cover 501 and the winding post 502 are connected to each other.

Further, a notch of each elastic groove 511 is provided with a convex tooth 515, and the outer cover 101 is provided with an internal spline 102 matched with the convex tooth 515. The limited block 503 is limited by the internal spline 102, so that the rotation of the winding post 502 without external force is effectively avoided. When the winding post 502 needs to rotate, because the elastic groove 511 is deformed elastically, an external force is applied to the operating cover 501 to make the elastic groove 511 deformable, the convex tooth 515 elastically moves away from the internal spline 102, and the rotation of the winding post 502 is realized.

Figure 2:
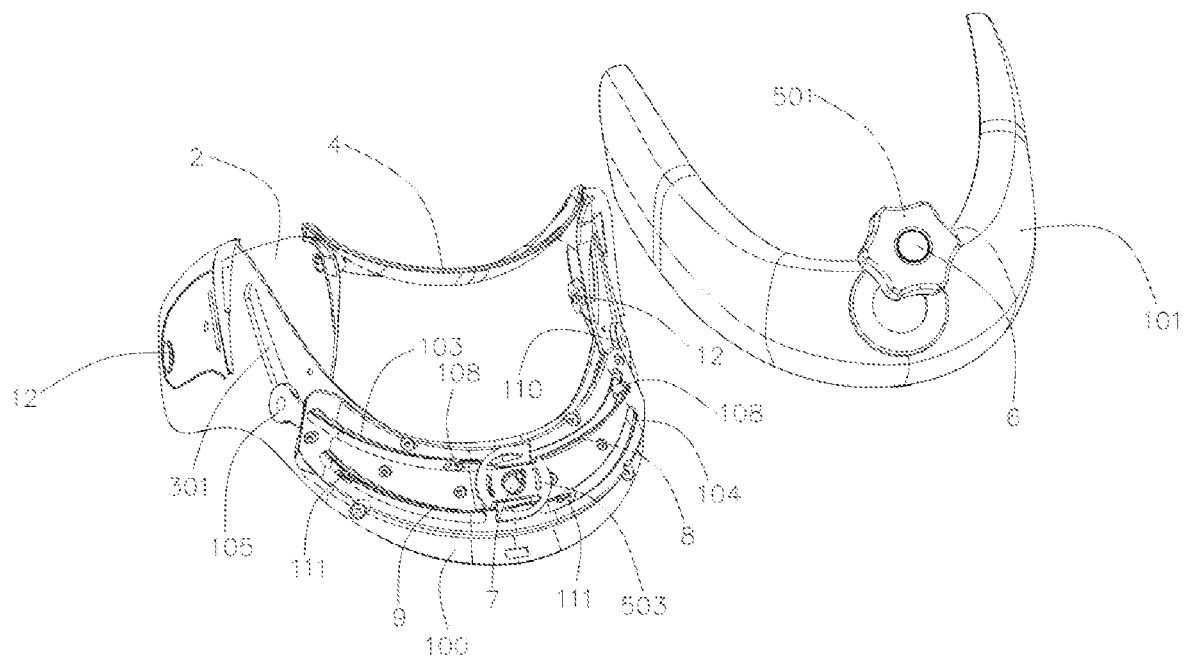
FIG. 2 is a partial stereoscopic exploded view of an adjustable neck support of the application.
Figure 3:
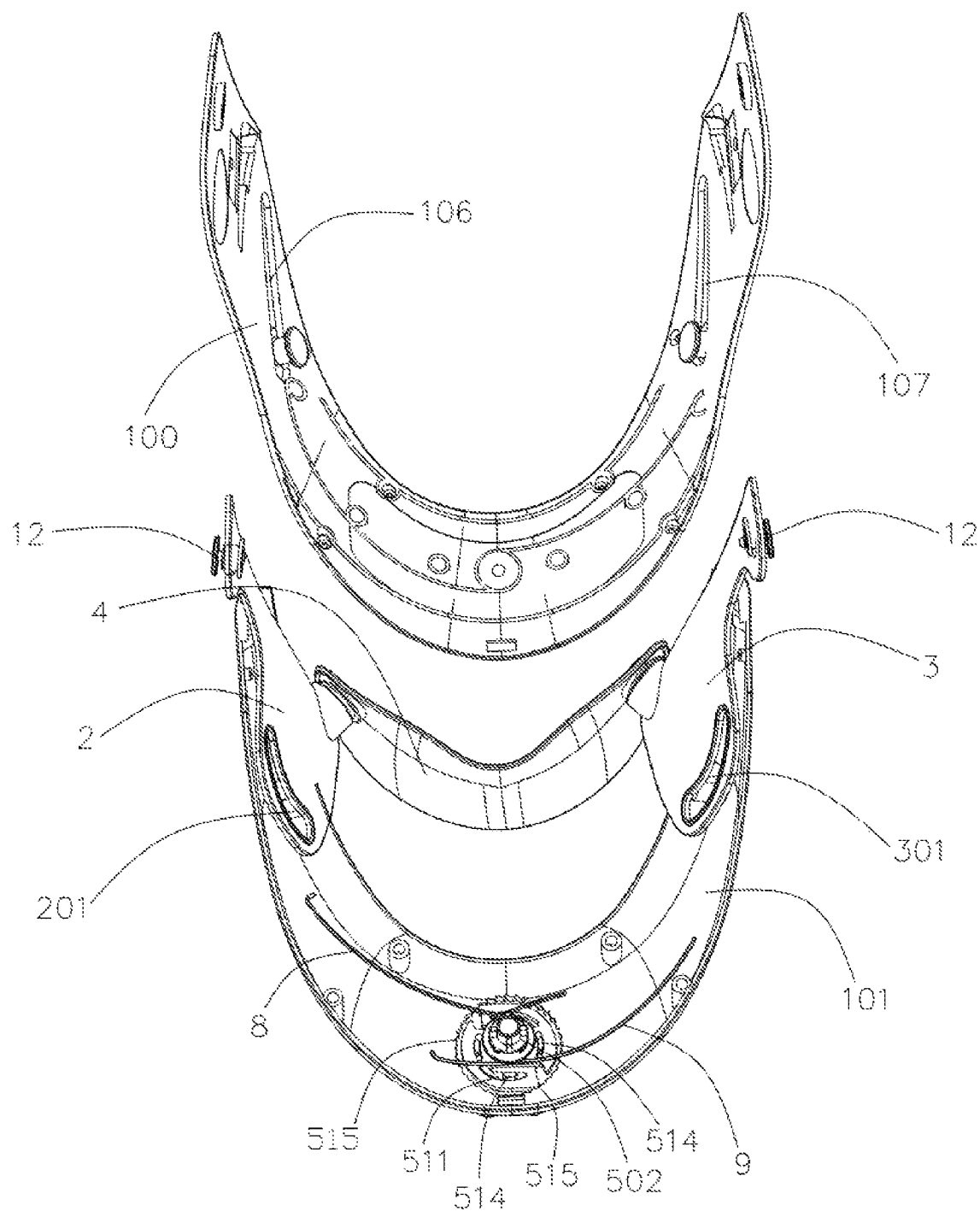
FIG. 3 is a stereoscopic exploded view of an adjustable neck support of the application.

As shown in FIG. 2 to FIG. 4, the bottom shell 100 is provided with a first chute 103 and a second chute 104, and the height adjustment knob 5 is located between the first chute 103 and the second chute 104. The first sliding block 10 is slidably mounted in the first chute 103, and the second sliding block 11 is slidably mounted in the second chute 104. The first sliding block 10 is provided with a first connecting head 105, and the second sliding block 11 is provided with a second connecting head 110. One end of the left side plate 2 is rotatably connected to the left end of the bottom shell 100 through a rotating piece 12, and the other end is provided with a left chute 201. One end of the right side plate 3 is rotatably connected to the right end of the bottom shell 100 through another rotating piece 12, and the other end is provided with a right chute 301.

Further, the left end of the bottom shell 100 is provided with a third chute 106, and the right end is provided with a fourth chute 107. The first connecting head 105 penetrates through the third chute 106 and the left chute 201, one face of the first connecting head 105 abuts against the left end of the bottom shell 100, and the other face abuts against the left side plate 2. The second connecting head 110 penetrates through the fourth chute 107 and the right chute 301, one face of the second connecting head 110 abuts against the right end of the bottom shell 100, and the other face abuts against the right side plate 3. Therefore, the left side plate 2 and the right side plate 3 are movably connected to the neck holder front support 1 respectively.

In addition, the first sliding block 10 is provided with two first joint pins 108. One first joint pin 108 is located at the tail of the first sliding block 10, and the other first joint pin 108 is located in the middle of the first sliding block 10. The second sliding block 11 is provided with two second joint pins 111. One second joint pin 111 is located at the tail of the second sliding block 11, and the other second joint pin 111 is located in the middle of the second sliding block 11. Both ends of the first cable 8 are fixed to the two first joint pins 108 respectively, and both ends of the second cable 9 are fixed to the two second joint pins 111 respectively. The first cable 8, the second cable 9, the first sliding block 10, and the second sliding block 11 are contained in a space defined by the bottom shell 100 and the outer cover 101. The first connecting head 105 and the second connecting head 110 extend out of the neck holder front support 1.

A working principle of the adjustable neck support of the application is as follows.

Through the rotation of the operating cover 501, the winding post 502 is driven to rotate to pull both ends of the first cable 8 and both ends of the second cable 9, so that the first sliding block 10 and the second sliding block 11 slide in opposite directions in the first chute 103 and the second chute 104 respectively, that is, the first sliding block 10 and the second sliding block 11 move towards each other or move away from each other.

At the same time, the first connecting head 105 slides in the third chute 106 and left chute 201, and the second connecting head 110 slides in the fourth chute 107 and right chute 301, thereby synchronously pushing up or pulling down the left side plate 2 and the right side plate 3. Then the left side plate 2 and the right side plate 3 push or pull the lower jaw holder plate 4 to realize the height adjustment of the neck support, so that the neck support is suitable for the patients with different neck lengths.

Compared with a traditional gear and rack adjustment structure, the smoothness of operation is effectively improved, so that the height adjustment is easier to operate, and the service life of the neck support is prolonged.

In conclusion, according to the adjustable neck support provided by the application, the height adjustment knob 5 is provided with the first cable 8 and the second cable 9. The first cable 8 is connected to the first sliding block 10, the first sliding block 10 is connected to the bottom shell 100 and the left side plate 2, the second cable 9 is connected to the second sliding block 11, and the second sliding block 11 is connected to the bottom shell 100 and the right side plate 3. When the height is adjusted, through the rotation of the operating cover 501, the winding post 502 is driven to rotate to pull both ends of the first cable 8 and both ends of the second cable 9, so that the first sliding block 10 and the second sliding block 11 slide in opposite directions in the first chute 103 and the second chute 104 respectively. The first connecting head 105 slides in the third chute 106 and the left chute 201, and the second connecting head 110 slides in the fourth chute 107 and the right chute 301, thereby synchronously pushing up or pulling down the left side plate 2 and the right side plate 3. Then the left side plate 2 and the right side plate 3 push or pull the lower jaw holder plate 4 to realize the height adjustment of the neck, so that the neck support is suitable for the patients with different neck lengths. Compared with the traditional gear and rack adjustment structure, the smoothness of operation is effectively improved, so that the height adjustment is easier to operate, and the service life of the neck support is prolonged.

Embodiment 2

Figure 10:
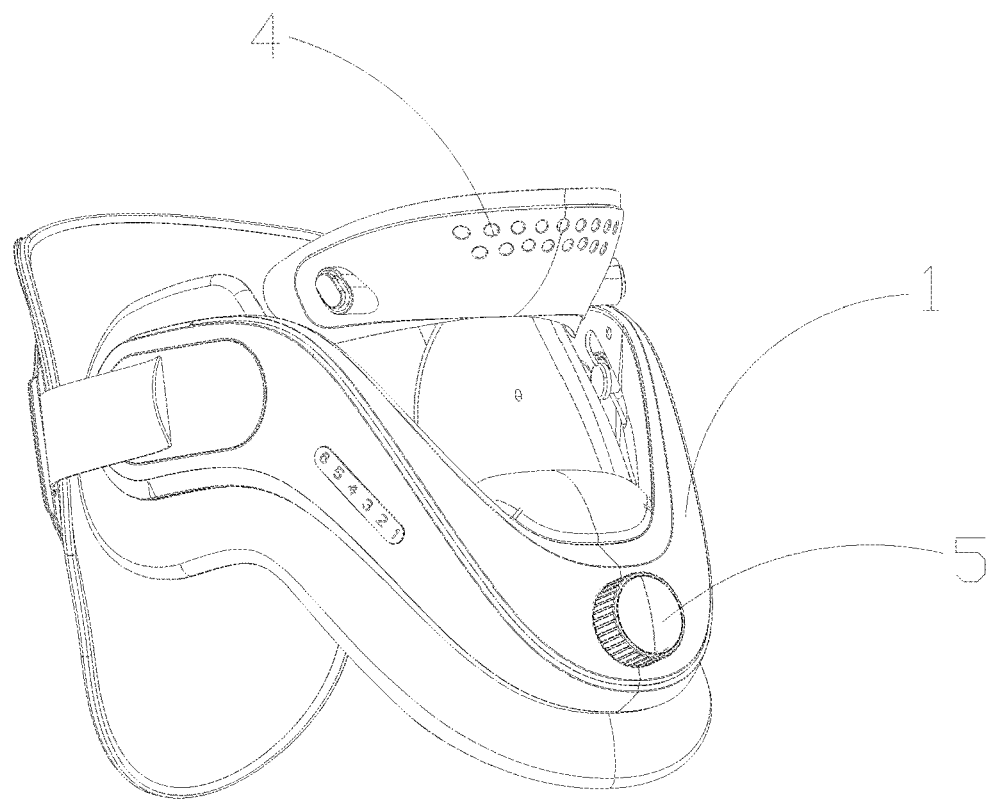
FIG. 10 is a stereoscopic view of embodiment 2 of an adjustable neck support of the application.
Figure 11:
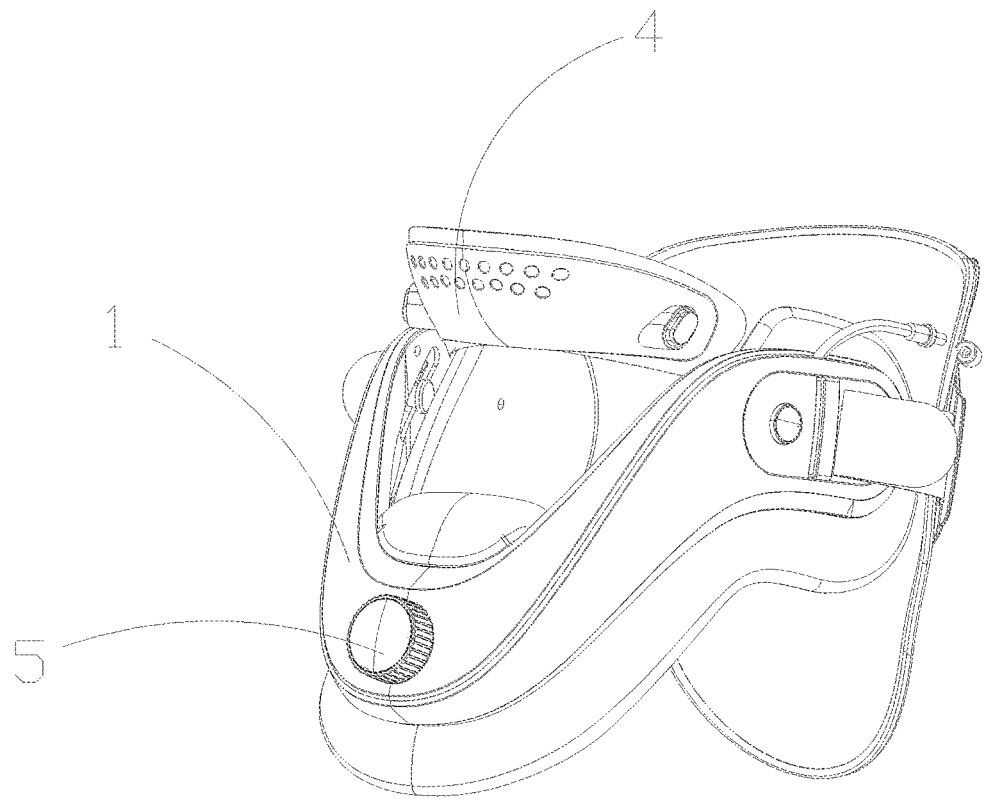
FIG. 11 is a stereoscopic view from another perspective of embodiment 2 of an adjustable neck support of the application.

As shown in FIGS. 10 and 11, this embodiment demonstrates another implementation of an adjustable neck support. The difference between embodiment 2 and embodiment 1 is that the left side plate, right side plate, and front bracket of the adjustable neck support are integrated, and the height of the mandibular bracket is adjusted by a height adjustment knob, making the adjustable neck support suitable for patients with different neck lengths.

The various embodiments of the application are combined arbitrarily, and should also be regarded as the content disclosed in the application without departing from the conception created by the application. Various simple modifications are made to the technical solutions and different embodiments are combined arbitrarily without departing from the conception created by the application within the scope of the technical conception of the application, which should be within the scope of protection of the application.

What is claimed is:

1. An adjustable neck support, comprising a neck holder front support, a left side plate, a right side plate, a lower jaw holder plate, and a height adjustment knob, wherein the left side plate and the right side plate are movably connected at a left end and a right end of the neck holder front support respectively, the lower jaw holder plate is connected between the left side plate and the right side plate, and the height adjustment knob is mounted on the neck holder front support; the height adjustment knob comprises an operating cover and a winding post connected to the operating cover; the winding post is mounted in the neck holder front support, and the operating cover exposes the neck holder front support;

a first sliding block and a second sliding block are slidably mounted in the neck holder front support, the first sliding block is provided with a first connecting head, and the second sliding block is provided with a second connecting head; the first connecting head is slidably connected to the left end of the neck holder front support and the left side plate, the second connecting head is slidably connected to the right end of the neck holder front support and the right side plate, a first cable and a second cable are wound on the winding post, both ends of the first cable are fixed to the first sliding block, and both ends of the second cable are fixed to the second sliding block;

the winding post is provided with a limited block and an extension part; the limited block is matched with the neck holder front support, and the operating cover is connected to the limited block; a first winding groove and a second winding groove are formed at both sides of the extension part respectively; the winding post is provided with a first threading hole and a second threading hole; the first threading hole is located in the first winding groove, the first cable penetrates through the first threading hole, and the first cable is wound in the first winding groove; and the second threading hole is located in the second winding groove, the second cable penetrates through the second threading hole, and the second cable is wound in the second winding groove; the neck holder front support is provided with a first chute and a second chute, and the winding post is located between the first chute and the second chute; and the first sliding block is slidably mounted in the first chute, and the second sliding block is slidably mounted in the second chute; the limited block is provided with two mounting grooves and two elastic grooves; the two mounting grooves are oppositely arranged, the two elastic grooves are oppositely arranged, and each elastic groove is arranged adjacent to each mounting groove; a connecting part protrudes from a bottom of the operating cover, the connecting part is provided with four limited posts, two of the limited posts are located in the two mounting grooves respectively, and other two limited posts are located in the two elastic grooves respectively; a notch of each elastic groove is provided with a convex tooth, and the neck holder front support is provided with an internal spline matched with the convex tooth; the neck holder front support comprises a bottom shell and an outer cover connected to the bottom shell; the connecting part is provided with a mounting hole, a nut is mounted in the mounting hole, and the winding post is mounted on the bottom shell; and a screw penetrates through the winding post, one end of the screw abuts against the bottom shell, and the other end is connected to the nut, and the operating cover abuts against the outer cover; one end of the left side plate is rotatably connected to a left end of the bottom shell, and other end of the left side plate is provided with a left chute; one end of the right side plate is rotatably connected to a right end of the bottom shell, and other end of the right side plate is provided with a right chute; the left end of the bottom shell is provided with a third chute, and the right end of the bottom shell is provided with a fourth chute; the first connecting head penetrates through the third chute and the left chute, one face of the first connecting head abuts against the left end of the bottom shell, and other face of the first connecting head abuts against the left side plate; and the second connecting head penetrates through the fourth chute and the right chute, one face of the second connecting head abuts against the right end of the bottom shell, and other face of the second connecting head abuts against the right side plate.

2. The adjustable neck support according to claim 1, wherein the first sliding block is provided with two first joint pins, one first joint pin is located at the tail of the first sliding block, and the other first joint pin is located in the middle of the first sliding block, and both ends of the first cable are fixed to the two first joint pins respectively.

3. The adjustable neck support according to claim 1, wherein the second sliding block is provided with two second joint pins, one second joint pin is located at the tail of the second sliding block, and the other second joint pin is located in the middle of the second sliding block, and both ends of the second cable are fixed to the two second joint pins respectively.

4. The adjustable neck support according to claim 1, wherein the first winding groove is provided with a first limiting groove, a first limit sleeve is mounted on the first cable, and the first limit sleeve is contained in the first limiting groove; and the second winding groove is provided with a second limiting groove, a second limit sleeve is mounted on the second cable, and the second limit sleeve is contained in the second limiting groove.

* * * * *